United States Patent [19]

Bell et al.

[11] 3,939,179

[45] Feb. 17, 1976

[54] CONTINUOUS PRODUCTION OF THIOPHENE FROM BUTANE

[75] Inventors: Thomas Robert Bell, Devon; Perrin Gary Smith, Chester Springs, both of Pa.

[73] Assignee: Pennwalt Corporation, Philadelphia, Pa.

[22] Filed: Aug. 29, 1973

[21] Appl. No.: 392,594

[52] U.S. Cl. ............................................. 260/332.8
[51] Int. Cl.$^2$ ......................................... C07D 333/10
[58] Field of Search .................................. 260/332.8

[56] References Cited
UNITED STATES PATENTS

| | | | |
|---|---|---|---|
| 2,562,238 | 7/1951 | Lukasiewicz | 260/332.2 |
| 2,694,074 | 11/1954 | Kemp | 260/332.8 |
| 2,694,075 | 11/1954 | Ruidisch | 260/332.8 |

FOREIGN PATENTS OR APPLICATIONS

| | | | |
|---|---|---|---|
| 632,306 | 11/1949 | United Kingdom | 260/332.8 |
| 633,239 | 12/1949 | United Kingdom | 260/332.8 |
| 887,426 | 1/1962 | United Kingdom | 260/332.8 |

*Primary Examiner*—Natalie Trousof
*Attorney, Agent, or Firm*—Robert G. Danehower

[57] ABSTRACT

Thiophene is continuously produced by reacting normal butane or a normal butene and hydrogen sulfide at elevated temperatures over a dehydrogenation catalyst, said reaction being conducted in the presence of sulfur vapor introduced in an amount to maintain the elevated reaction temperature and to overcome the heat loss caused by the endothermic reaction between the $C_4$ hydrocarbon and hydrogen sulfide.

The mole ratio of hydrogen sulfide to $C_4$ hydrocarbon must be maintained within the range of 15 to 20 moles of hydrogen sulfide per mole of n-butane or n-butene. Conversions may vary from 60 to 20% per pass depending on catalyst activity. This requires that unreacted $C_4$ hydrocarbon and hydrogen sulfide be recirculated. Carbon disulfide is a by-product of the reaction along with nominal amounts of other materials.

4 Claims, No Drawings

CONTINUOUS PRODUCTION OF THIOPHENE FROM BUTANE

BACKGROUND OF THE INVENTION

The production of thiophene from by-product refinery gases by reacting hydrogen sulfide or sulfur with n-butane, n-butylene and butadiene has been studied for many years. One of the early refinery processes as disclosed in U.S. Pat. No. 2,450,658 reacted butane or butylene with sulfur at temperatures within the range of 1100° to 1300°F. in a stainless steel reactor tube to produce thiophene and tar residues. In this non-catalytic process almost as much by-product tar was produced as the desired thiophene.

In U.S. Pat. No. 2,450,659 the inventors in describing the reaction of butane and sulfur in the vapor phase noted that the reaction proceeds with extreme speed, the only limitation apparently being the rapidity with which heat can be supplied to the reaction mixture.

In U.S. Pat. No. 2,558,507 the patentees reacted butylene with hydrogen sulfide over alumina catalyst to produce thiophene. In U.S. Pat. No. 2,570,722 the patentees reacted butylene with a mixture of sulfur dioxide and hydrogen sulfide over dehydrogenation catalysts to produce thiophene.

In U.S. Pat. No. 2,694,074 the patentees reacted butylene with a mixture of hydrogen sulfide and a thermally labile sulfur compound over a dehydrogenation catalyst to produce thiophene. In a similar reaction described in U.S. Pat. No. 2,694,075 butane was reacted with hydrogen sulfide over a dehydrogenation catalyst to produce thiophene. In this reaction catalyst contact time was in the range of 0.2 to 2 seconds and at a mole ratio of 0.5 to 6 moles of hydrogen sulfide per mole of butane. Catalyst life was in the order of about 75 minutes.

The production of thiophene from butane or butene and hydrogen sulfide is also made difficult by the extremely corrosive conditions encountered at reaction temperatures which cause excessive reactor metal loss. This is particularly true where large amounts of heat must be transferred through reactor walls to overcome the heat loss due to endothermic reactions. These problems were observed in U.S. Pat. No. 2,562,238 where butane was reacted with sulfur to produce thiophene and tars.

BRIEF DESCRIPTION OF THE INVENTION

N-butane, n-butene, or a mixture thereof, hereinafter referred to as $C_4$ hydrocarbon, is preheated to 500°–900°F. and then passed into a reactor containing a bed of dehydrogenation catalyst. Hydrogen sulfide and sulfur vapor are preheated to 900°–1100°F. and then passed into the reactor where they mix with the $C_4$ hydrocarbon gas and then the mixed gases pass through the dehydrogenation catalyst. Both the $C_4$ hydrocarbon and hydrogen sulfide feed streams will contain recycled portions since complete reaction is not obtained, and in addition, hydrogen sulfide is used at a large molar excess.

The reactor may conveniently be a cylinder packed with catalyst. The exterior reactor wall is insulated to prevent heat loss to the atmosphere. The reactor may be constructed of ceramic materials such as Varnon and Duro brick in order to avoid metal failure due to excessive corrosion encountered at the high reaction temperature.

The mole ratio of hydrogen sulfide to $C_4$ hydrocarbon is maintained within the range of 20 to 1 to 15 to 1. The sulfur rate is regulated so that the temperature in the catalyst bed is maintained within the range of 900°F. to 1100°F., with higher sulfur rates raising the catalyst bed temperature and lower sulfur rates lowering the catalyst bed temperature. The catalyst space velocity defined as volume of reactants per volume of packed catalyst space per hour is not important in the operation to the process except as it bears on the sizing of the catalytic reactor. The catalyst may be any dehydrogenation catalyst inert to the reaction.

The reactor gas effluent will contain thiophene, hydrogen sulfide, unreacted butane, carbon disulfide and smaller amounts of materials such as hydrogen, methane, butylene, butadiene, mercaptans, sulfur, and tars. The various materials are separated, for example, by distillation with the $C_4$ hydrocarbon and hydrogen sulfide recycled to the reactor. The thiophene product and carbon disulfide by-product may be purified by distillation and sold as commercial grade products.

The reaction is continued until the conversion of $C_4$ hydrocarbon to thiophene drops below about twenty percent per pass. Catalyst on-stream life averages about 150 hours of operation after which the catalyst is regenerated.

The catalyst is regenerated by passing flue gas through the catalyst bed for a sufficient time to burn off the carbon and to restore catalyst activity. The flue gas is composed principally of air, nitrogen and a small amount of carbon dioxide. The flue gas can be preheated as necessary to maintain a catalyst bed temperature of about 1400° to 1600°F. during regeneration. About 25 hours of regeneration treatment are required to restore the catalyst activity.

DETAILED DESCRIPTION OF THE INVENTION

This invention is directed to the reaction of hydrogen sulfide with one or more members of the class consisting of normal butane, 1-butene and 2-butene, which are the normal butenes, in the presence of a dehydrogenation catalyst to produce thiophene, carbon disulfide and hydrogen. The n-butane, 1-butene and 2-butene as well as mixtures thereof will be referred to hereafter as $C_4$ hydrocarbon. Butadiene can be used in the same reaction, either by itself or in admixture with one or more of the other $C_4$ hydrocarbons but its high cost generally precludes its use for this reaction. The reaction is carried out in the range of 900° to 1100°F., preferably in the range 950° to 975°F. Since the reaction is quite endothermic heat transfer through reactor walls or heat exchanger tubes must take place in order to maintain the high reaction temperature. Our first two cylindrical reactors, one made of type 304 stainless steel and the second made of type 446 stainless steel failed after 24 hours and 50 hours respectively.

In accordance with this invention, we then discovered that if we introduced sufficient sulfur into the reaction zone along with the $C_4$ hydrocarbon and hydrogen slufide, we were able to operate the reaction adiabatically, that is without external heat. This adiabatic reaction simplified our reactor construction problems permitting use of ceramic reactors instead of metal since we no longer needed to replace the heat lost due to the endothermic hydrogen sulfide reaction. We believe the reaction temperature is maintained by a preferential exothermic reaction of sulfur with the generated hydrogen rather than sulfur with the $C_4$ hydrocarbon. This preferential reaction is believed to be determined by the high mole ratio of hydrogen sulfide to $C_4$ hydrocarbon required in our process. This mole ratio of hydrogen sulfide to $C_4$ hydrocarbon should be in the range of 15 to 20 and preferably is in the range of 18 to 20. Low conversion of $C_4$ hydrocarbon to thiophene is observed at mole ratios under 15.

Both the $C_4$ hydrocarbon feed and the hydrogen sulfide feed to the reactor will contain substantial quantities of recycle gases since conversion of the $C_4$ hydrocarbon to thiophene seldom exceeds sixty percent per pass. The sulfur vapor is conveniently introduced to the reactor by mixing it with the hydrogen sulfide stream. The mixed sulfur-hydrogen sulfide stream passes through a preheater to bring it near reaction temperature, i.e., within the range of 900° to 1100°F. Preferably, the reaction temperature is maintained within the range of 950° to 975°F. for optimum production of thiophene and minimum production of carbon disulfide which is produced simultaneously with thiophene. If it is desired to increase the proportion of carbon disulfide and decrease the thiophene we operate the catalyst bed at the higher end of the 900° to 1100°F. temperature range, that is from 1000°F. to 1100°F.

The sulfur feed rate is adjusted to the minimum amount necessary to maintain the reaction temperature within the range of 900° to 1100°F. under adiabatic conditions. The sulfur is kept to the minimum amount since excess sulfur tends to cause blockages in reactor product lines. Generally, the sulfur to $C_4$ hydrocarbon weight ratio is about 0.95 to 1.8 pounds of sulfur per pound of n-butane while a preferred ratio is about 1.22 to 1. For a normal butene the ratio is about 0.57 to 1.1 pounds of sulfur per pound of n-butene. The reactant gas streams can be mixed inside the reactor before contact with the catalyst or the reactants can be individually directed into the catalyst zone.

We have operated our process for producing thiophene in a vertical cylindrical reactor having a fixed bed of solid contact catalyst with down-through reactant streams and product flow. However, the catalytic reaction zone may be in a horizontal reactor and it can also be of the fluid bed type in which type of operation the catalyst is maintained in powder form in a turbulent state.

We have found that Varnon and Duro brick manufactured by Harbison-Walker are satisfactory construction materials for our adiabatic thiophene reactor.

We have found that any inert solid contact catalyst of the dehydrogenation type is satisfactory to practice our invention. The catalytic dehydrogenation of $C_4$ hydrocarbon supplies the hydrogen for reaction with sulfur. The catalyst must also promote cyclicization to thiophene. A preferred group of catalysts includes compounds of the metals nickel, cobalt, platinum, vanadium, chromium, molybdenum, palladium, manganese, magnesium, tungsten, zinc, tantalum, aluminum and the like. Suitable compounds of these metals are the oxides, sulfides, carbonates, chromates chromites, molybdates, tungstates, sulfo-molybdates, sulfo-tungstates and the like. Nonmetallic solid catalysts such as charcoal and silica gel may be impregnated with the metal compounds noted above. The catalytic agent may be in the form of a powder, granules, pellets etc. or deposited on a carrier which may be inert or another dehydrogenation catalyst. The catalysts may be used severally, or in admixture with each other or with inert materials.

Another preferred group of dehydrogenation catalysts is the amphoteric metal oxides and sulfides which are stable under reaction conditions. Examples are the oxides of aluminum, chromium, vanadium, molybdenum, titanium, magnesium, boron, and silicon and sulfides of nickel, tungsten, cobalt, tin, etc. as well as mixtures thereof. Specific catalysts which have been successful in our process include 19 percent manganese dioxide on alumina, 14 percent nickel oxide on alumina, 20 percent molybdenum sulfide on alumina, 10 percent molybdenum trioxide on alumina, 2 percent potassium oxide-19 percent chromium oxide on alumina, 19 percent chromium oxide on alumina, 2 percent nickel oxide-19 percent chromium oxide on alumina, 1 percent iron oxide-19 percent chromium oxide on alumina, 50 percent cobalt molybdate on alumina, 0.3 percent palladium on alumina, 17.5 percent chromium oxide on alumina, and 18.2 percent chromium oxide on alumina.

The space velocity of the reactants in the catalyst does not affect the chemistry of the process and may be operated within the range of about 200 to about 1800 volumes of reactants at operating conditions per volume of packed catalyst space per hour. Most of the time, we operated at a space velocity of about 790 and this is preferred. This provided a contact time of the reactants with the catalyst of about 2.3 seconds.

The dehydrogenation catalysts have a period of optimum activity after which the conversion of butane to thiophene per pass gradually decreases. We have used a 19 percent chromium oxide on alumina catalyst for periods lasting over 400 hours. As the catalyst decreases in activity the volume of the recycle streams become progressively larger and more difficult to handle. In general, we found that if we shut down when the conversion to thiophene dropped below about 50 percent per pass based on new butane charged to the reaction we obtained an average of about 150 hours of on-stream time before reactivating the catalyst.

The catalyst is reactivated or regenerated by contacting the catalyst with oxygen in the presence of an inert gas at elevated temperatures. The oxygen can be supplied as an air-nitrogen mixture or as flue gas comprising air, carbon dioxide and nitrogen or an air-stream mixture. The preferred regeneration gas is flue gas which is inexpensive and which normally contains nitrogen, oxygen and carbon dioxide.

Regeneration temperatures are held within the range of about 1400° to 1600°F. The time required for catalyst regeneration will be determined empirically and will depend on the length of catalyst on stream time, the volume of regenerating gas per cubic foot of catalyst and the temperature of the air going into the catalyst bed. A 19 percent chromium oxide catalyst which had been on stream for 402 hours was regenerated with flue gas in 50.5 hours. At a later cycle of the same catalyst, 25 hours were required for regeneration after the catalyst was on stream for 158.5 hours. Regeneration temperatures averaged between 1450° and 1550°F.

The conversion of $C_4$ hydrocarbon to thiophene will vary from a high of 60 percent per pass with a freshly regenerated catalyst and will gradually decrease with continued on stream time until it reaches a point where it is more economical to regenerate the catalyst. The process of our invention is not affected by pressure and any convenient pressure may be used.

The reactor product stream contains about 90 percent hydrogen sulfide, 4 percent C₄hydrocarbons-principally butane, 4 percent thiophene, 1 percent carbon disulfide and 1 percent miscellaneous materials consisting of hydrogen, methane, ethylene, ethane, mercaptans and high boiling liquids and gases. The hydrogen, methane, ethane, and ethylene are vented from the system in a gas stream. The hydrogen sulfide and $C_4$ hydrocarbons are recycled to the reactor. The carbon disulfide and thiophene are separated by distillation or by other procedures and purified as desired.

The process of the invention may be further illustrated by the following examples. These examples are different periods of continuous operation in which the following procedure and equipment were utilized.

EXAMPLE 1

Twenty five pounds of 19 percent chromium oxide on alumina catalyst, Harshaw Chemical Co. catalyst no. Cr 0205T, size 5/32 inch tablets having an apparent bulk density of 60 pounds per cubic foot were placed in a ceramic lined cylindrical vessel having a diameter of 6 inches. The packing occupied 23 inches of the reactor equivalent to 0.376 cu. ft. The reactor was carefully insulated to assure adiabatic reaction conditions.

Separate feed lines were piped to the top of the reactor to introduce sulfur vapor and hydrogen sulfide in one line and $C_4$ hydrocarbon in the second line. The reactor product gas left the bottom of the reactor and passed through a ceramic packed tower where the gas stream was scrubbed with a liquid stream of organic sulfur compounds to remove any excess sulfur and high boiling sulfur compounds and then it was passed through silica gel drying towers. The scrubbed gas was then cooled and routed to a cyclonic separator where additional high boiling liquids were removed.

The reactor gas was then compressed to about 275 p.s.i.g. and partially liquefied. The hydrogen, methane, ethylene, ethane, and propylene were removed as overhead and burned. The liquid bottoms were fed to a distillation column for complete removal of hydrogen sulfide as the overhead stream at 250 p.s.i.g. and 80°F. overhead temperature.

The liquid bottoms from this column were then fed into a second distillation column where $C_4$ hydrocarbons were taken as the overhead stream at 100°F. and 30 p.s.i.g. The liquid bottoms contained the thiophene and carbon disulfide. These two products were separated by distillation.

The $C_4$ hydrocarbon recycle stream from the distillation column was returned to the reactor by way of a preheater. Fresh $C_4$ hydrocarbon was added as required. The overhead hydrogen sulfide stream was recirculated to the reactor through a preheater.

Sulfur powder was charged to a melting pot and the liquid sulfur was pumped into the recirculating hydrogen sulfide. This stream then entered a preheater where the sulfur vaporized before entering the reactor.

Operating in the manner described above 42,179 grams of crude thiophene were produced over a period of 168 hours without regeneration of catalyst. Production and operating figures at 8 hour intervals as well as total production figures are given in Table 1.

Table 1

| | Continuous Production of Thiophene | | | | | | | | | |
|---|---|---|---|---|---|---|---|---|---|---|
| Time (Hours) | 16 | 24 | 32 | 40 | 48 | 56 | 64 | 72 | 80 | 88 |
| Reactants | | | | | | | | | | |
| 1) Sulfur (grams) | 3760 | 3760 | 3760 | 3760 | 3760 | 3760 | 3760 | 3760 | 3760 | 3760 |
| 2) Butane (grams) | | | | | | | | | | |
| Fresh | 1784 | 1801 | 1784 | 1801 | 1801 | 1801 | 1784 | 1847 | 1756 | 1671 |
| Recycled | 773 | 193 | 657 | 1256 | 1043 | 1495 | 1005 | 1043 | 676 | 1642 |
| In H₂S | 36 | | 226 | | 145 | 145 | 291 | 363 | 363 | 400 |
| Total | 2593 | 1994 | 2667 | 3057 | 2989 | 3441 | 3080 | 3253 | 2795 | 3713 |
| 3) Hydrogen Sulfide (grams) | | | | | | | | | | |
| Recycled | 35,885 | 35,957 | 32,002 | 36,006 | 35,957 | 36,175 | 35,594 | 35,957 | 35,884 | 35,775 |
| Mole Ratio – $\frac{H_2S}{C_4H_{10}}$ | 23.6 | 30.7 | 20.5 | 20.1 | 20.5 | 17.9 | 19.7 | 18.9 | 21.9 | 10.4 |
| Catalyst Bed Temp. °F. | | | | | | | | | | |
| Maximum | 942 | 945 | — | 940 | 940 | 940 | 938 | 940 | 938 | 930 |
| Minimum | 915 | 920 | — | 920 | 925 | 925 | 925 | 930 | 925 | 915 |
| Products | | | | | | | | | | |
| 1) Light Gases Vented (cu. ft.) | 63 | 49 | 49 | 71 | 57.6 | 33 | 57.8 | 23.7 | 19.4 | 87.4 |
| 2) High Boiling Sulfur Compounds (grams) | — | — | — | — | — | — | — | — | — | — |
| 3) Crude Thiophene (grams) | 2744 | 2484 | 2193 | 2110 | 2487 | 2485 | 2410 | 3390 | 2734 | 2168 |
| % Thiophene | 74.8 | 61.2 | 63.5 | 62.3 | 64.0 | 66.3 | 69.7 | 69.2 | 71.0 | 71.7 |
| Thiophene (grams) | 2052 | 1520 | 1392 | 1314 | 1591 | 1647 | 1679 | 1653 | 1976 | 1554 |
| % Carbon Disulfide | 24.4 | 37.5 | 45.6 | 38.5 | 34.1 | 33.0 | 28.8 | 28.6 | | 27.7 |
| Carbon Disulfide (grams) | 669 | 931 | 780 | 801 | 848 | 820 | 696 | 685 | 779 | 600 |
| Conversion of Butane to Thiophene (%) | 54.6 | 52.6 | 36.0 | 29.7 | 36.7 | 33.0 | 37.6 | 35.1 | 48.8 | 28.9 |

| Time (Hours) | 96 | 104 | 112 | 120 | 128 | 136 | 144 | 152 | 160 | 168 | Av./8 hrs. | Totals (grams) |
|---|---|---|---|---|---|---|---|---|---|---|---|---|
| Reactants | | | | | | | | | | | | |
| 1) Sulfur (grams) | 3760 | 3760 | 3760 | 3760 | 3760 | 3760 | 3760 | 3760 | 3760 | 3760 | 3760 | 75,200 |
| 2) Butane (grams) | | | | | | | | | | | | |
| Fresh | 1422 | 1722 | 1490 | 1371 | 1654 | 1325 | 1257 | 1631 | 1773 | 1756 | 1662 | 33,242 |
| Recycled | 1855 | 1391 | 2029 | 1120 | 1352 | 1043 | 1314 | 618 | 695 | 927 | 1106 | 22,132 |
| In H₂S | 363 | 719 | 863 | 621 | 647 | 315 | 289 | 610 | 1048 | 1084 | 426 | 8,526 |
| Total | 3640 | 3832 | 4382 | 3112 | 3653 | 2683 | 2860 | 2859 | 3516 | 3767 | 3195 | 63,902 |
| 3) Hydrogen Sulfide (grams) | | | | | | | | | | | | |
| Recycled | 35,884 | 35,238 | 35,094 | 35,845 | 35,238 | 30,896 | 35,704 | 34,987 | 34,620 | 34,693 | 35,172 | 703,451 |
| Mole Ratio – $\frac{H_2S}{C_4H_{10}}$ | 16.8 | 15.7 | 13.7 | 19.6 | 16.5 | 19.6 | 21.3 | 20.9 | 16.8 | 15.7 | 19.3 | |
| Catalyst Bed Temp. °F. | | | | | | | | | | | | |
| Maximum | 932 | 930 | 950 | 960 | 940 | 955 | 950 | 970 | — | 950 | | |

Table 1-continued

Continuous Production of Thiophene

| | | | | | | | | | | | | |
|---|---|---|---|---|---|---|---|---|---|---|---|---|
| Minimum | 915 | 925 | 940 | 950 | 940 | 960 | 940 | 950 | — | 940 | | |
| Products | | | | | | | | | | | | |
| 1) Light Gases Vented (cu. ft.) | 58.3 | 86 | 63 | 63 | 116 | 81.2 | 78.4 | 12.2 | 11.2 | 50 | 56.5 | 1130.2 |
| 2) High Boiling Sulfur Compounds (grams) | — | — | 1904 | — | 2621 | — | — | 1257 | — | 4211 | — | 9993 |
| 3) Crude Thiophene (grams) | | | | | | | | | | | | |
| % Thiophene | 75.7 | 77.3 | 80.4 | 80.0 | 77.5 | 78.7 | 73.8 | 74.3 | 77.0 | 81.2 | 72.5 | |
| Thiophene (grams) | 1783 | 1646 | 1595 | 1412 | 1443 | 1114 | 1031 | 1168 | 1356 | 1364 | 1514 | 30,295 |
| % Carbon Disulfide | 21.5 | 20.3 | 17.6 | 16.2 | 20.4 | 18.8 | 20.9 | 24.1 | 18.9 | 16.3 | 25.6 | |
| Carbon Disulfide (grams) | 506 | 432 | 349 | 286 | 380 | 266 | 292 | 379 | 332 | 275 | 555 | 11,108 |
| Conversion of Butane to Thiophene (%) | 33.8 | 29.7 | 25.1 | 31.3 | 27.3 | 28.7 | 24.9 | 28.2 | 26.6 | 25.0 | 33.7 | |

Average yields from the above period calculated as weight percent of total normal butane feed were thiophene-49 percent, carbon disulfide-16.3 percent, hydrogen sulfide-90.5 percent, light gases-2.7 percent and high boiling sulfur compounds-7.0 percent.

The gaseous mixture entering the catalytic reactor bed had the following average composition expressed as weight percent: sulfur-8.78 percent, hydrogen sulfide-84 percent, $C_4$ hydrocarbons-7.16 percent, carbon disulfide-0.05 percent and mercapto compounds-0.001 percent.

The gaseous mixture leaving the catalytic reactor bed and entering the scrubber system had the following average composition expressed as percent by weight: light gases-0.1 percent, hydrogen sulfide-91.0 percent, $C_4$ hydrocarbons-3.6 percent, carbon disulfide-1.23 percent, mercapto compounds-0.001 percent, thiophene-3.53 percent and high boiling sulfur compounds-0.50 percent.

EXAMPLE 2

Following the procedures of Example 1, continuous production of thiophene took place for 136 hours without regeneration of catalyst. Mole ratios of hydrogen sulfide to butane ranged from 20 to 12. Poor conversion of butane to thiophene was observed at mole ratios lower than 15. Operating data for the 80 through 136 hour period are presented in Table 2.

Table 2

Continuous Production of Thiophene

| Time (Hours) | 88 | 94 | 102 | 110 | 118 | 126 | 136 |
|---|---|---|---|---|---|---|---|
| Reactants | | | | | | | |
| 1) Sulfur (grams) | 3816 | 3816 | 3816 | 3816 | 3816 | 3816 | 3816 |
| 2) Butane (grams) | | | | | | | |
| Fresh | 1730 | 1646 | 1476 | 1702 | 1475 | 1702 | 1589 |
| Recycled | 614 | 522 | 682 | 808 | 1161 | 1896 | 1761 |
| In $H_2S$ | 588 | 605 | 974 | 579 | 209 | 931 | 967 |
| Total | 2932 | 2773 | 3132 | 3089 | 2845 | 4529 | 4317 |
| 3) Hydrogen Sulfide (grams) | | | | | | | |
| Recycled | 30,880 | 32,067 | 31,707 | 31,975 | 32,436 | 31,753 | 31,720 |
| Mole Ratio — $\frac{H_2S}{C_4H_{10}}$ | 18.2 | 19.7 | 17.3 | 17.6 | 19.5 | 12.0 | 12.5 |
| Catalyst Bed Temp. °F. | | | | | | | |
| Maximum | 950 | 955 | 950 | 965 | — | 952 | 938 |
| Minimum | 958 | 970 | 960 | 945 | — | 970 | 950 |
| CUZ,1/6 Products | | | | | | | |
| 1) Light Gases Vented (cu. ft.) | 14.34 | 12.63 | 7.93 | 7.56 | 7.90 | 8.62 | 8.43 |
| 2) High Boiling Sulfur Compounds (grams) | — | 858 | 901 | 630 | 1343 | 694 | — |
| 3) Crude Thiophene (grams) | | | | | | | |
| % Thiophene | 71.8 | 70.6 | 68.4 | 73.2 | 75.6 | 73.0 | 75.6 |
| Thiophene (grams) | 1636 | 2038 | 1380 | 1363 | 1241 | 1211 | 1340 |
| % Carbon Disulfide | 27.2 | 28.5 | 28.9 | 25.9 | 24.2 | 23.8 | 22.3 |
| Carbon Disulfide (grams) | 619 | 580 | 583 | 482 | 397 | 395 | 395 |
| Conversion of Butane to Thiophene (%) | 38.5 | 35.8 | 30.4 | 30.5 | 30.1 | 18.5 | 21.5 |

EXAMPLE 3

The chromium oxide on alumina catalyst was replaced with ⅜ inch ceramic ring packing to observe conversion of normal butane to thiophene without a dehydrogenation catalyst. The observed conversions to thiophene were 40 percent lower than with the catalyst. High boiling sulfur compounds formed initially and steadily increased in proportion when operating at 950° to 1000° F. When the reactor bed temperature was increased to 1050°F we observed a further increase in the proportion of high boiling sulfur compounds with no increase in the yield of thiophene. The entire run conducted over a period of seven days encountered numerous shutdowns because of blockages from unreacted sulfur.

EXAMPLE 4

Using 19 percent chromium oxide catalyst on alumina base, Harshaw Chemical's Cr 1404T, size ⅛ inch pellets and following the procedure of Example 1, we were able to operate for 402 hours without regeneration. The run was discontinued when the weight percent conversion of fresh butane dropped below 50 percent.

EXAMPLE 5

Following the procedure set forth in Example 1, but using Harshaw Chemical's Cr 1404T catalyst (chromium oxide on alumina) we operated for 236 hours before shutting down for reactivation of catalyst. The catalyst was reactivated by passing 60 cu. ft/hour of nitrogen mixed with 8 cu. ft./hour of air through the catalyst bed. The maximum catalyst bed temperature was 1400° to 1450°F. Temperatures were maintained by increasing the air flow to raise the temperature and lowering the air flow to lower the temperature. When the temperature dropped off the reactivation was completed.

EXAMPLE 6

Following the procedure described in Example 1 we produced thiophene over a chromium oxide-alumina catalyst for 402 hours before the conversion of fresh n-butane dropped below 50 percent on a weight basis. The catalyst was reactivated by passing flue gas containing 7 percent carbon dioxide, 53.5 percent nitrogen and 39.5 percent air on a volume basis. This gas was introduced at 46.8 cu. ft./hour and it maintained a catalyst bed temperature of 1500°F. in the reactor, averaging about 1480° to 1550°F. When the temperature dropped to 1450°F. the air flow was increased. Regeneration required 50.5 hours. After using the same catalyst for 158.5 hours, the catalyst was regenerated with flue gas in the manner described above in 25 hours.

EXAMPLE 7

Using a laboratory scale reactor the following catalysts were tried in the conversion of $C_4$ hydrocarbon to thiophene:

19 percent manganese dioxide on alumina. At a 20 to 1 mole ratio of hydrogen sulfide to butene-1, and at a temperature of 878°F. a 59 weight percent conversion to thiophene was observed. Gas contact time with the catalyst was 1.5 seconds.

14 percent nickel oxide on alumina. At a catalyst temperature of 807°F. and a 20 to 1 mole ratio of hydrogen sulfide to butene-1, a product was obtained comprising 43 percent by weight thiophene and 28 percent by weight carbon disulfide. Catalyst contact time was 3.5 seconds.

20 percent molybdenum sulfide on alumina. At a temperature of 932°F. hydrogen sulfide at a 18 to 1 mole ratio to butane was passed over the catalyst at a contact time of 3.3 seconds with 45 weight percent conversion to thiophene.

10 percent molybdenum trioxide on alumina. At 18 to 1 mole ratio of hydrogen sulfide to n-butane a 35 percent conversion to thiophene was observed. Catalytic activity decreased after 20 hours of reaction.

2 percent potassium oxide/19 percent chromium oxide on alumina. At a catalyst bed temperature of 1075°F. and 20 to 1 mole ratio of hydrogen sulfide to butene-1 conversions to thiophene were excellent and excelled those obtained with chromium oxide on alumina catalyst. After 56 hours of operation, the catalyst was regenerated with air. Upon resuming operations, catalyst activity was 10 percent less than previously observed.

2 percent nickel sulphate/19 percent chromium oxide/aluminum oxide. Conversion of butene-1 to thiophene was 10 percent less than that obtained with the same catalyst without the nickel.

1 percent iron oxide/19 percent chromium oxide/alumina. At a temperature of 932°F. this catalyst was considerably less active than the same catalyst without the iron. 35 percent conversion to thiophene from butene-1 was obtained.

0.3 percent palladium on aluminum oxide. The highest conversion to thiophene with this catalyst was 14.5 percent at a temperature of 752°F.

18.2 percent chromium oxide on alumina. This catalyst showed about a 60 percent conversion to thiophene from butene-1 after 20 hours of operation.

We claim:

1. In a continuous catalytic gas-phase process of reacting hydrogen sulfide with one or more $C_4$ hydrocarbons selected from the group consisting of normal butane, normal butenes and mixtures thereof to produce thiophene, by-product carbon disulfide and by-product hydrogen comprising continuously preheating the said $C_4$ hydrocarbon reactant within the range 500° to 900°F. and separately preheating the hydrogen sulfide reactant within the range of 900° to 1100°F. and thereafter introducing the said reactant gases to a dehydrogenation catalytic reactor maintained at a temperature within the range of 900° to 1100°F.

continuously withdrawing a product stream from the said reactor containing thiophene, carbon disulfide, hydrogen, excess hydrogen sulfide and unreacted $C_4$ hydrocarbons, separating thiophene and carbon disulfide from the reactor product stream while recycling excess hydrogen sulfide and unreacted $C_4$ hydrocarbons to the said reactor and regenerating the dehydrogenation catalyst when the conversion to thiophene falls off, the improvement consisting of introducing the said reactant gases at a mole ratio of hydrogen sulfide to $C_4$ hydrocarbon ranging from about 15 to 1 to about 20 to 1 to an adiabatic reactor containinng a dehydrogenation catalyst while simultaneously introducing sulfur vapor to the catalyst to react with by-product hydrogen and thereby to generate heat in an amount sufficient to maintain the catalyst temperature within the range of 900° to 1100°F.

2. The process of claim 1 in which the catalyst bed temperature is maintained within the range of 950° to 975°F.

3. The process of claim 1 in which the $C_4$ hydrocarbon is normal butane and the amount of sulfur vapor introduced to the catalyst bed ranges from 0.95 to 1.8 pounds of sulfur per pound of normal butane introduced.

4. The process of claim 1 in which the $C_4$ hydrocarbon is a normal butene and the amount of sulfur vapor introduced to the catalyst bed ranges from 0.57 to 1.1 pounds of sulfur per pound of normal butene introduced.

* * * * *